United States Patent [19]

Morris et al.

[11] Patent Number: 4,609,762

[45] Date of Patent: Sep. 2, 1986

[54] THIOETHERS HAVING A HIGH SULFUR CONTENT AND METHOD THEREFOR

[75] Inventors: Lester Morris, Encino; Hakam Singh, Arcadia; Jonathan D. Zook, North Hollywood, all of Calif.

[73] Assignee: Products Research & Chemical Corp., Glendale, Calif.

[21] Appl. No.: 575,263

[22] Filed: Jan. 30, 1984

[51] Int. Cl.[4] ............................................. C07C 148/00
[52] U.S. Cl. ..................................... 568/38; 528/373; 528/375; 528/390
[58] Field of Search .................. 568/38; 528/373, 375, 528/390

[56] References Cited

U.S. PATENT DOCUMENTS

| | | | |
|---|---|---|---|
| 3,705,882 | 12/1972 | Skillicorn | 528/373 |
| 4,366,307 | 12/1982 | Singh et al. | 528/373 |

FOREIGN PATENT DOCUMENTS

| | | | |
|---|---|---|---|
| 683154 | 3/1964 | Canada | 528/373 |
| 683698 | 4/1964 | Canada | 528/373 |
| 710404 | 5/1965 | Canada | 528/373 |

*Primary Examiner*—Joseph L. Schofer
*Assistant Examiner*—N. Sarofim
*Attorney, Agent, or Firm*—Poms, Smith, Lande & Rose

[57] ABSTRACT

Liquid polythioethers containing no oxygen in the polymeric backbone and a method for producing same which includes condensing an organic compound having primary mercaptan group with an organic compound having secondary hydroxyl group beta to a sulfur atom.

36 Claims, No Drawings

THIOETHERS HAVING A HIGH SULFUR CONTENT AND METHOD THEREFOR

BACKGROUND OF THE INVENTION

Elastomers prepared from liquid polymers which exhibit good fuel, water and temperature resistance are very important commercial products. One way the prior art has attempted to produce such polymers is by condensing sodium polysulfide and dichloroethyl formal. The resulting polymer and many disadvantages including acid and water sensitivity and limited elevated temperature resistance. Improved fuel resistance has been achieved with ether-thioether polymers made by condensing beta-thioether alcohols in the presence of acid catalysts, e.g. as shown in U.S. Pat. No. 4,366,307. Such condensation is achieved by using high temperatures (e.g., 150° C. or higher) and intense dehydration. Moreover, it is impossible, using polyols, to eliminate the oxygen in the polymeric backbone or to obtain directly mercaptan terminals during condensation and it is very difficult to increase the sulfur to oxygen ratio in the polymer which, we have found, increases the polymer's resistance to water.

U.S. Pat. No. 3,317,486 discloses the reaction between mercaptoethanol and the mixture of alpha and beta-mercaptopropanol. This reaction, according to the patent, produces a solid copolymer of randomly distributed isomers along the backbone. In column 3, lines 37–41, it is stated that regardless of which isomer is used the copolymer will be substantially the same.

The '486 patent preferably uses an approximately equimolar ratio of reactants but irrespective of the ratio, the patent states that the resulting copolymer is a solid, generally either waxy or powdery, and cannot be vulcanized. Moreover, the solid polymers produced by this patent have one terminal mercaptan group and one terminal hydroxyl group and therefore, even if liquid, these polymers could not be cured by any common commercial

SUMMARY OF THE INVENTION

The present invention is based upon the surprising finding that a relatively low temperatures and in the presence of a strong acid dehydration catalyst a primary mercaptan group will condense with a hydroxyl group if the hydroxyl group is a secondary hydroxyl and located beta to a sulfur atom. It is very important that the hydroxyl group be secondary since we have found that a secondary hydroxyl group, if beta to a sulfur atom, is more reactive with a primary mercaptan than a correspoding primary hydroxyl group located beta to a sulfur atom. The condensation reaction proceeds very smoothly with substantially no oxidation of the mercaptan groups and no cyclization by-products; in fact, yields of the desired product approach 100%. Using this reaction, a liquid polymer is produced having no unsaturation in the polymeric backbone.

The reaction produces many desirable products including high molecular weight liquid polythioethers (both linear and branched). The unique reaction allows one to vary the ratio of sulfur to oxygen widely depending on the properties desired of the final polythioether. Surprisingly, liquid polythioethers which contain no oxygen and are mercaptan terminated can be directly produced by the condensation reaction. This is a great improvement over U.S. Pat. No. 4,366,307 in which mercaptan terminated polymers can not be made directly. Moreover, excluding oxygen from the backbone not only increases fuel resistance but also greatly increases the water resistance of the polymer. In general, the liquid polythioethers produced by the method of the present invention are non-crystallizing, have a water, solvent, fuel and temperature resistant backbone, and can have a variety of end groups which make the solid polythioethers useful for a wide variety of applications. For example, depending on the end group, the liquid polythioethers are vulcanizable to elastomers which are water, solvent, fuel and temperature resistant and exhibit elastomeric properties over a wide range of temperature.

By "non-crystallizing" we mean a polymer which is liquid at ambience and is not a semi-crystalline wax, gum or solid. Moreover, the non-crystallizing polymer, even when cooled to a sufficiently low temperature to become a solid, will be an amorphous solid which, when the temperature is raised to ambience, will return to the liquid state. It is noted that when we state that the hydroxyl group is located beta to a sulfur atom we mean that the hydroxyl group is separated from a sulfur atom by two carbon atoms. By "secondary hydroxyl" we mean that the carbon atom, to which the hydroxyl is attached, has one hydrogen atom and two other organic groups which are not hydrogen. By "primary mercaptan" we mean that the carbon atom, to which the mercaptan group is attached, also has two hydrogen atoms.

The liquid polythioethers described above, as well as certain monomers, may be produced by condensing primary mercaptan terminated organic compounds having no other chemically reactive groups with organic compounds having secondary hydroxyl groups beta to a sulfur atom and having no other chemically reactive groups. Alternatively, the secondary hydroxyl group and primary mercaptan group may be on the same molecule (hereinater secondary beta-hydroxyl mercaptan) in which event the secondary beta-hydroxyl mercaptan compound will self-condense in the presence of an appropriate initiator to form a liquid polythioether having either hydroxyl or mercaptan terminals.

The liquid polythioethers of the present invention may also be easily made by condensing an organic compound having two terminal secondary hydroxyl groups each located beta to a sulfur atom and no other chemically reactive groups (hereinafter di-secondary beta-thiodiol) with an organic compound having two primary mercaptan groups but no other chemically reactive groups (hereinafter organic primary dimercaptan). If an excess of the organic dimercaptan is used there is produced a mercaptan terminated liquid polythioether which can be easily cured to a solid elastomeric rubber and exhibits excellent water, solvent, fuel and temperature resistance. Liquid polythioethers having terminal hydroxyl groups are produced if an excess of the di-secondary beta-thiodiol is used. In this reaction using the special conditions set out infra, the hydroxyl groups do not condense with each other which was very surprising to us in view of their high reactivity.

Chain extended dihydroxy monomers in which each hydroxy group is located beta to a sulfur atom (hereinafter beta-thioether diol) are also easily made by the method of the present invention by condensing an organic compound having two beta hydroxyl groups, one or both being secondary hydroxy, but containing no other chemically reactive groups, with an organic compound terminated by one primary mercaptan group and one primary beta-hydroxyl group and containing no other chemically reactive groups (hereinafter beta-mercaptan alcohol). It is noted that the hydroxyl may be located beta to the mercaptan group or any other sulfur atom. The beta-thioether diols are very useful since they may be condensed using the method described in U.S. Pat. No. 4,366,307, to produce liquid polythioethers which may be cured to solid elastomers with high sulfur to oxygen ratios.

To produce a branched liquid polythioether there should be included with the other reactants an organic triol or tetrol branching agent or tri- or tetramercaptan branching agent, neither branching agent having any other chemically raective groups, each of the hydroxyl groups on the branching agent being secondary and located beta to sulfur atom and each mercaptan group being primary. The branching agent may have the formula:

$$R''—(Z)_q$$

wherein q is 3 or 4 and R" is a tri- or tetravalent organic radical having no chemically reactive groups, Z is a secondary hydroxyl located beta to a sulfur atom or is a primary mercaptan group.

By "chemically reactive groups" we mean groups which do not react under the conditions of our method. Such "chemically reactive groups" include disulfide linkages, ether linkages, halide groups, and ester linkages.

DESCRIPTION OF THE PREFERRED EMBODIMENTS

The di-secondary beta-thioether diols useful in the condensation reaction will in general have the following formula:

$$HO—CH—CH—S—(R—S)_p—CH—CH—OH$$
$$\phantom{HO—}|\phantom{CH}|\phantom{—S—(R—S)_p—}|\phantom{CH}|$$
$$\phantom{HO—}R_1\phantom{C}R_2\phantom{—S—(R—S)_p—}R_3\phantom{C}R_4$$

wherein each of $R_2$ and $R_3$ is hydrogen or lower alkyl, each of $R_1$ and $R_4$ is lower alkyl, R is lower alkylene or lower alkylene thioether and p is 0 to 3.

The organic primary dimercaptan, useful in the condensation reaction, will have the following formula:

$$R'—(SH)_2$$

wherein R' is any organic divalent radical having no chemically reactive groups and is preferably lower alkylene, lower alkylene thioether, lower alkyl aryl, or lower alkyl heterocyclic.

The condensation reaction using the di-secondary beta-thioether diol and organic primary dimercaptan will produce high molecular weight liquid polythioethers (the molecular weight will vary between about 900 to as high as is possible and still obtain a liquid—about 20,000 or 25,000—, the particular molecular weight being largely a matter of choice). The liquid polythioethers formed during the condensation reaction will be mercaptan terminated and have no oxygen in the backbone when an excess or organic primary dimercaptan is used. Such polythioethers are highly desirable because the lack of oxygen and increase in sulfur in the backbone increases water and fuel resistance and the mercaptan terminals are easily vulcanized if a branched liquid polythioether is produced. The general formula for such liquid polythioethers is as follows:

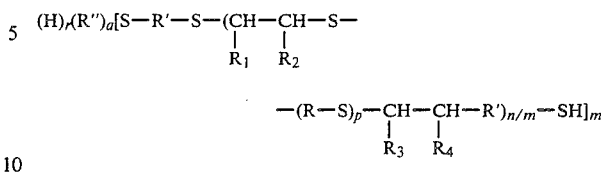

wherein R, R', $R_1$, $R_2$, $R_3$, $R_4$ and p have the same meaning as indicated hereinbefore, R" is a tri- or tetravalent organic radical having no chemically reactive groups of the branching agent $R''(Z)_q$ wherein Z is secondary hydroxyl located beta to a sulfur atom or primary mercaptan, n is from about 8 to 200, q is 3 or 4, r is 0 or 1, a is 0 or 1, the sum of r and a being 1, m is 1, 3, or 4, when m is 1, r is 1 and when m is 3 or 4, a is 1.

The liquid polythioethers formed during the reaction of the di-secondary beta-thioether diol and the organic primary dimercaptan will be hydroxyl terminated if an excess of di-secondary beta-thioethers is used. Such hydroxyl terminated polythioethers can be linear or branched depending on whether or not the branching agent $R''—(Z)_q$ is used.

The general formula for the hydroxy terminated liquid polythioether is as follows:

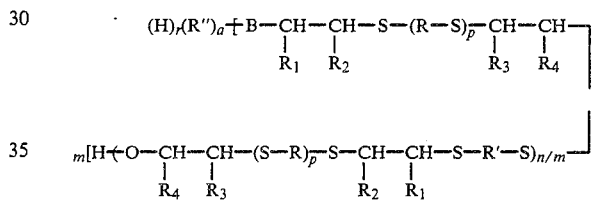

wherein R, a, p, n, m, $R_1$, $R_2$, $R_3$, $R_4$, R', and R" have the same meaning as indicated hereinbefore and B is oxygen if Z is hydroxyl, and sulfur if Z is mercaptan.

The hydroxyl terminated polythioethers can be used as described in U.S. Pat. No. 4,366,307.

In addition to the foregoing, the condensation method of our invention may also produce liquid polythioethers having a molecular weight of about 900 to about 20,000 or 25,000 by the self-condensation of a secondary beta-hydroxyl mercaptan in the presence of an organic polymercaptan initiator, the number of terminal mercaptan groups being 2, 3 or 4, all of which are primary, or with an organic polyhydroxy initiator, the number of terminal hydroxyl groups being 2, 3 or 4 all of which are secondary and beta to a sulfur atom, neither initiator having any chemical reactive groups other than the hydroxy or mercaptan groups, respectively. In general, the secondary beta-hydroxy mercaptan will have the formula:

$$HO—CH—CH—S—(H)_t(R'''—SH)_u$$
$$\phantom{HO—}|\phantom{CH}|$$
$$\phantom{HO—}R_5\phantom{C}R_6$$

wherein —SH is primary, $R_5$ is lower alkyl, $R_6$ is hydrogen or lower alkyl, t and u are each 0 or 1 the sum of u and t being 1, when t is 1, $R_6$ is hydrogen, and R''' is a divalent organic radical such as lower alkylene or lower alkylene thioether having no chemically reactive groups.

The organic polyhydroxy initiator will in general have the formula:

$$R^{iv}—(OH)_s$$

wherein $R^{iv}$ is a di-, tri- or tetravalent organic compound having no chemically reactive groups, s is 2, 3 or 4 and each of the —OH groups are secondary and beta to a sulfur atom. If the initiator has two hydroxyl groups a linear polythioether having two terminal hydroxy groups is produced. If the initiator has three or four hydroxyl groups the resulting liquid polythioether will be branched and have three or four terminal hydroxyl groups. Such linear or branched liquid polythioethers may be used in the same manner as those disclosed in U.S. Pat. No. 4,366,307.

The polymercaptan initiator, in which each mercaptan group is primary will in general have the formula:

$$R^v—(SH)_w$$

wherein $R^v$ is an organic radical having no chemically reactive groups, the —(SH) groups are primary and w is 2, 3 or 4. The resulting liquid polythioether will be mercaptan terminated and will be branched if w is 3 or 4. Such mercaptan liquid polythioethers are easily vulcanized to a solid rubber elastomer using conventional oxidizing agents such as dichromates or peroxides.

The reaction of the secondary beta-hydroxyl mercaptan and the polyhydroxy initiator may be exemplified as follows:

$$nHO—\underset{R_5}{CH}—\underset{R_6}{CH}—S—(H)_t—(R'''—SH)_u + R^{iv}(OH)_s$$

$$\downarrow$$

$$R^{iv}—[[(S—R''')_u—S—\underset{R_6}{CH}—\underset{R_5}{CH}]_{n/s}—OH]_s + nH_2O$$

wherein n, $R_5$, $R_6$, t, u, $R^{iv}$ and s have the same meaning as indicated hereinbefore.

The reaction between the secondary beta-hydroxyl

-continued

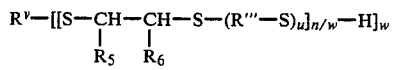
$$R^v—[[S—\underset{R_5}{CH}—\underset{R_6}{CH}—S—(R'''—S)_u]_{n/w}—H]_w$$

wherein n, $R_5$, $R_6$, t, $R'''$, u, $R^v$ and w have the same meaning as indicated hereinbefore.

The condensation reaction of our invention can also produce beta-hydroxyl terminated monomers (beta-thioether diols) which will self-condense or condense with other beta-thioether diols, e.g. as disclosed in U.S. Pat. No. 4,366,307, to form liquid polythioethers using the method set forth in this patent.

The beta-thioether diols of this invention are produced by reacting an organic compound having two beta hydroxyl groups, one of which is secondary and one of which is primary (mono-secondary beta-thiodiol) or a di-secondary beta-thiodiol with a beta-mercaptan alcohol, both the mercaptan and the alcohol group being primary. It is important that the alcohol (hydroxyl) group be primary in order to prevent self-condensation since the primary hydroxyl group is less reactive with the primary mercaptan group than is a secondary hydroxyl group. In any event, the general formula of the beta mercaptan alcohols is as follows:

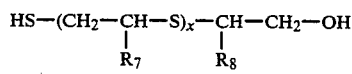
$$HS—(CH_2—\underset{R_7}{CH}—S)_x—\underset{R_8}{CH}—CH_2—OH$$

wherein $R_7$ is hydrogen or lower alkyl, $R_8$ is hydrogen or lower alkyl, x is 0 or 1 and when x is 0, $R_8$ is hydrogen.

The mono-secondary beta-thiodiol will in general have the formula:

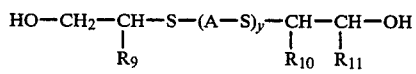
$$HO—CH_2—\underset{R_9}{CH}—S—(A—S)_y—\underset{R_{10}}{CH}—\underset{R_{11}}{CH}—OH$$

wherein each of $R_9$ and $R_{10}$ is hydrogen or lower alkyl, $R_{11}$ is lower alkyl, A is lower alkylene or thioloweralkylene and y is 0 or 1.

The reaction between the mono-secondary beta thiodiol and the beta mercaptan alcohol is as follows:

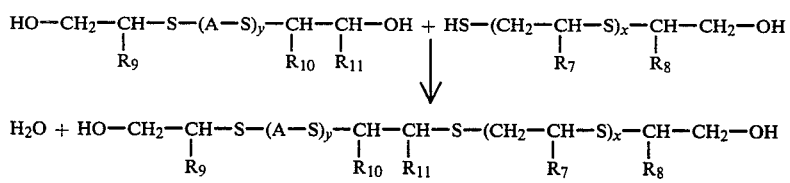

$$HO—CH_2—\underset{R_9}{CH}—S—(A—S)_y—\underset{R_{10}}{CH}—\underset{R_{11}}{CH}—OH + HS—(CH_2—\underset{R_7}{CH}—S)_x—\underset{R_8}{CH}—CH_2—OH$$

$$\downarrow$$

$$H_2O + HO—CH_2—\underset{R_9}{CH}—S—(A—S)_y—\underset{R_{10}}{CH}—\underset{R_{11}}{CH}—S—(CH_2—\underset{R_7}{CH}—S)_x—\underset{R_8}{CH}—CH_2—OH$$

mercaptan and the polymercaptan initiator may be exemplified as follows:

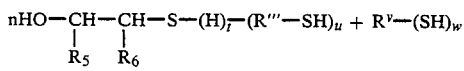
$$nHO—\underset{R_5}{CH}—\underset{R_6}{CH}—S—(H)_t—(R'''—SH)_u + R^v—(SH)_w$$

$$\downarrow$$

wherein $R_7$, $R_8$, $R_9$, $R_{10}$, $R_{11}$, A, x and y have the same meaning as indicated hereinbefore.

The reaction between the beta mercaptan alcohol and the di-secondary beta-thiodiol is as follows:

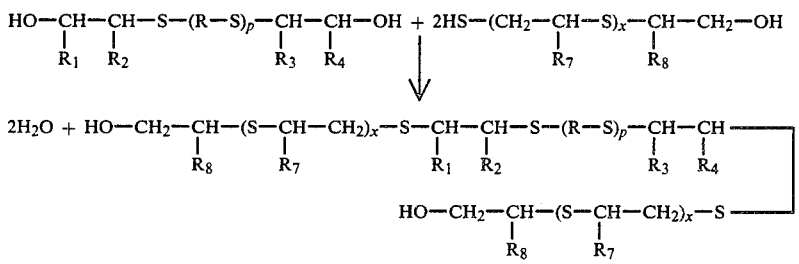

wherein $R_1$, $R_2$, $R_3$, $R_4$, $R_7$, $R_8$, R, p and x have the same meaning as indicated hereinbefore.

The above-described condensation reactions take place at relatively low temperatures in the presence of a catalytic effective amount of a non-oxidizing strong acid dehydration catalyst.

The temperature of the reaction must be below about 140° C. and preferably between about 90° C. to about 130° C. or 135° C.

The catalyst may be any strong acid, i.e. an acid which is a dilute aqueous solution, is substantially completely ionized, and which is non-oxidizing under the conditions of the reaction. As examples of non-oxidizing, strong acid dehydration catalysts there may be mentioned sulfuric acid, sulfonic acids, particularly aromatic sulfonic acids such as benzene or toluene sulfonic acids and polystyrene sulfonic acid.

In order that the strong acids be non-oxidizing there must be a sufficient amount of water present at all times, the amount of water necessary will vary depending on the acid. It should be noted that some strong acids, such as nitric acid and perchloric acid, are always oxidizing regardless of the amount of water present.

The amount of catalyst present is not particularly critical but it should not be present in such a large amount as to cause side reactions. In general, the amount of catalyst should be less than about 10 weight % and preferably will range from about 0.1 weight % to about 5 or 10 weight %, all percentages being based on the initial weight of the reactants.

Since the reaction of our invention is a condensation reaction water is formed during the reaction. Part of this water must be removed in order to prevent, inter alia, the reaction from terminating. This can be accomplished by allowing the water to distill off during the initial stages of the reaction and then gradually applying a vacuum when the reaction is nearing completion.

The strong acid may be removed be washing with dilute alkali.

The di-secondary beta-thioether diols may easily be made following the procedure set forth in U.S. Pat. No. 4,366,307. For example, such diols may be produced by reacting a dithiol with two moles of a lower alkyl substituted epoxide such as propylene oxide. Other di-secondary beta-thioether diols may be produced by reacting a secondary beta hydroxyl mercaptan with a lower alkyl substituted epoxide such as propylene oxide.

Exemplary of the di-secondary beta-thioether diols useful in the present invention and produced by the reactions indicated above are:

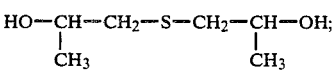

-continued

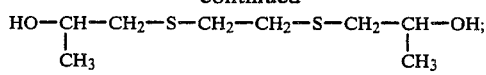

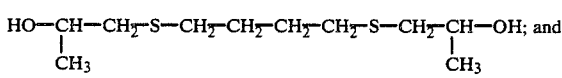

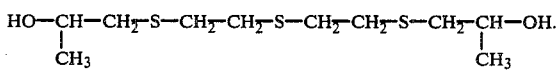

The organic primary dimercaptans useful in the present invention are, in general, well known in the art and include lower alkylene thioether dimercaptans, lower alkylene dimercaptans and aromatic dimercaptans such as alkyl aromatic and hetero-aromatic dimercaptans. Specific compounds which may be mentioned are:

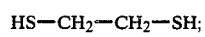

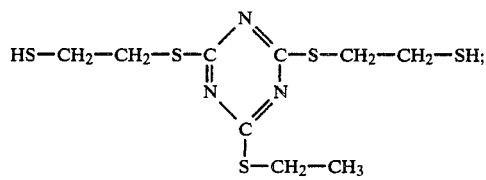

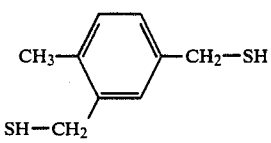

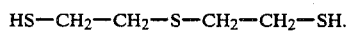

As has been noted hereinbefore the reaction of the di-secondary beta thioether diol and primary organic dimercaptan (when no branching agent is used) will produce linear liquid polythioethers which are mercaptan terminated if an excess (preferably about a molar excess) of primary organic dimercaptan is used and hydroxyl terminated if an excess (preferably about a molar excess) of di-secondary beta thioether diol is used.

In order to produce branched liquid polythioethers a branching agent is used having the general formula $R''-(Z)_q$ wherein q, $R''$ and Z have the same meaning as indicated hereinbefore.

The branching agent, when Z is hydroxyl, preferably has a molecular weight of less than about 500, has from 8 to 20 carbon atoms, contains no chemically reactive groups such as a disulfide linkage other than the hydroxyl groups.

Such triol branching agents may be made by the reaction of one mole of epichlorhydrin with two moles of the secondary beta hydroxy mercaptan. Compounds produced by this reaction have the formula:

$$HO-CH(R_5)-CH(R_6)-S-(R'''-S)_u-CH_2-CH(OH)-CH_2-(S-R''')_u-S-CH(R_6)-CH(R_5)-OH$$

wherein R''', R$_5$, R$_6$ and u have the same meaning as indicated above.

An exemplary compound is:

$$HO-CH(CH_3)-CH_2-S-CH_2-CH(OH)-CH_2-S-CH_2-CH(CH_3)-OH;$$

Tetrol branching agents may be made by reacting 2 moles of epichlorohydrin with 1 mole disodium salt of ethane dithiol and then adding mercaptopropanol to produce the following tetrol:

$$HO-CH(CH_3)-CH_2-S-CH_2-CH(OH)-CH_2-S-CH_2-CH_2-S-CH_2-CH(OH)-[HO-CH(CH_3)-CH_2-S-CH_2-]$$

The tri- and tetramercaptan branching agents, i.e. those branching agents of the above formula when Z is mercaptan preferably have molecular weight of less than 500 and R'' will be alkylene of from four to thirty carbon atoms, lower alkyl aryl and lower alkyl heterocyclic. Such tri- and tetra-mercaptan compounds include the following:

$$HS-CH_2-CH(CH_2-SH)-CH_2-SH;$$

$$HS-CH_2-C(CH_2-SH)(CH_2-SH)-CH_2-SH; \text{ and}$$

[triazine with three S-CH$_2$-CH$_2$-SH substituents]

The amount of branching agent used is not critical in the polymerization but is important in determining molecular weight and cross-link density. In general the amount will vary between about 0.1 mole % to about 5 mole % based on the total moles of di-secondary beta-thiodiol and organic primary dimercaptan.

The secondary beta-hydroxy mercaptan are known in the art and include the following:

$$HO-CH(CH_3)-CH_2-SH \text{ and}$$

$$HS-CH_2-CH_2-S-CH_2-CH_2-S-CH_2-CH(CH_3)-OH$$

As noted hereinbefore, such secondary beta hydroxy mercaptans will self-condense under the reaction conditions described hereinbefore in the presence of the organic polyhydroxy initiator or the organic polymercaptan initiator.

The polyhydroxy initiators having 3 or 4 hydroxyl groups may be the same as the triol or tetrol branching agent. The dihydroxy initiators may be the same as the di-secondary beta-thioether diols which have been set forth above.

The polymercaptan initiators having two primary mercaptan groups may be the same as the organic primary dimercaptan, specific compounds having been set out above. The tri- and tetra-mercaptans are, in general known in the art and may be the same as tri- and tetra-mercaptan branching agent.

The amount of initiator used in the reaction is not important for the reaction but does determine the molecular weight and may range from about 0.1 mole % to about 5 mole % based on the other reactants.

Beta-mercaptan alcohols useful in our invention include the following:

$$HS-CH_2-CH_2-OH;$$

$$HS-CH_2-CH_2-S-CH(CH_3)-CH_2-OH; \text{ and}$$

$$HS-CH_2-CH_2-S-CH_2-CH_2-OH.$$

Mono-secondary beta-thiodiols useful in our invention include:

$$HO-CH(CH_3)-CH_2-S-CH_2-CH_2-OH \text{ and}$$

$$HO-CH(CH_3)-CH_2-S-CH_2-CH_2-S-CH_2-CH_2-SH$$

The following examples are for the purpose of exemplification only and are not to be considered limiting.

EXAMPLE 1

Synthesis of linear thiol-terminated polythioether.

| | |
|---|---|
| 2,2'-Thiodipropanol | 953 grams |
| 2,2'-Dimercaptodiethyl sulfide | 1047 grams |
| Sulfuric acid (50% w/w) | 20 grams |

| | |
|---|---|
| Barium hydroxide (19.3 grams Ba(OH)₂.H₂O in 100 grams H₂O) | 119.3 grams |

Procedure:

The 2,2'-thiodipropanol, 2,2'-dimercaptodiethyl sulfide, and the sulfuric acid were stirred together under nitrogen in a 2 l. glass reactor fitted with a stirrer, thermometer, and fractionating distillation column. The temperature of the stirred material was brought to 100° C. and the water formed was allowed to distill. After five hours the mercaptan equivalent was 1000 g/eq. Further reaction was carried out under vacuum. After 2 hours analysis showed a mercaptan equivalent of 2100 g/eq. and no hydroxyl remaining in the infra-red spectra. The resulting polythioether was a slightly turbid, colorless liquid.

The barium hydroxide slurry was then added to the sulfuric acid containing polythioether. This mixture was stirred at 98° C. for approximately 3 hours or until analysis showed the mixture to be neutral. The polythioether polymer was dried and filtered to remove the barium sulfate formed. The neutralized polythioether was a slightly turbid, colorless liquid with a viscosity of 110 poise. The polythioether when mixed with a Novalac epoxy of functionality 2.2, cured to a rubber of 20 Rex.

EXAMPLE 2

Synthesis of chain extended dihydroxy monomer and condensation thereof to a linear thioalkyl terminated non-reactive polythioether.

| | |
|---|---|
| 2,2'-Thiodipropanol | 493 grams |
| Hydroxyethyl-2-hydroxy propyl sulfide (HE-2-HPS) | 447 grams |
| 2-Mercaptoethanol | 769 grams |
| 2-Hydroxyethylhexyl sulfidxe (HEHS) | 271 grams |
| Sulfuric Acid (50% w/w) | 20 grams |
| Barium Hydroxide (19.3 grams Ba(OH)₂.H₂O in 100 grams H₂O) | 119.3 grams |

Procedure:

The 2,2' thiodipropanol, 2-hydroxyethyl-2-hydroxypropyl sulfide, and the 50% sulfuric acid were stirred together under nitrogen in a 2 liter glass reactor fitted with a stirrer, thermometer, addition funnel and a fractionating distillation column. The temperature of the stirred material was rapidly brought to 100° C. at which point, the slow addition of a mixture of the 2-mercaptoethanol and the HEHS was begun. The addition was complete after 3 hours. The temperature was then increased to 120° C. and the water formed allowed to distill. When the mercaptan equivalent reached 33,000 g/eq, further reaction was carried out under vacuum until analysis showed a hydroxyl number of 10 or less. The resulting polythioether was a turbid, colorless liquid.

The barium hydroxide slurry was then added to the sulfuric acid containing polythioether. This mixture was stirred at 98° C. for approximately 3 hours or until analysis showed the mixture to be neutral. The polythioether polymer was then dried and filtered to remove the barium sulfate formed. The neutralized polythioether was a slightly turbid, colorless liquid with a viscosity of 48 poise. The molecular weight was 1800 as determined by gel permeation chromatography (hereinafter GPC).

EXAMPLE 3

Synthesis of chain extended dihydroxy monomer and condensation thereof to a linear thioalkyl terminated non-reactive polythioether.

| | |
|---|---|
| HE-2-HPS | 1096 grams |
| 2-Mercaptoethanol | 629 grams |
| HEHS | 275 grams |
| Sulfuric Acid (50% w/w) | 20 grams |
| Barium Hydroxide (19.3 grams Ba(OH)₂.H₂O in 100 grams H₂O) | 119.3 grams |

Procedure:

The HE-2-HPS and the sulfurci acid were stirred together under nitrogen in a 2 l. glass reactor fitted with a stirrer, thermometer, addition funnel and a fractionating distillation column. The temperature of the stirred material was rapidly brought to 100° C., at which point, the slow addition of a mixture of the 2-mercaptoethanol and the HEHS was begun. The addition was complete after 3 hours. The temperature was then increased to 120° C. and the water formed allowed to distill. When the mercaptan equivalent reached 33,000 g/eq, further reaction was carried out under vacuum until analysis showed a hydroxyl number of 10 or less. The resulting polythioether was a turbid, colorless liquid.

The barium hydroxide slurry was then added to the sulfuric acid containing polythioether. This mixture was stirred at 98° C. for approximately 3 hours or until analysis showed the mixture to be neutral. The polythioether polymer was then dried and filtered to remove the barium sulfate formed. The neutralized polythioether was a slightly turbid, colorless liquid with a viscosity of 60 poise and a molecular weight, as determined by GPC, of 1910.

EXAMPLE 4

Synthesis of chain extended dihydroxy monomer and condensation thereof to a linear thioalkyl terminated nonreactive polythioether.

| | |
|---|---|
| 2,2'-Thiodipropanol | 847 grams |
| 2-Mercaptoethanol | 880 grams |
| HEHS | 273 grams |
| Sulfuric Acid (50% w/w) | 20 grams |
| Barium Hydroxide (19.3 grams Ba(OH)₂.H₂O in 100 grams H₂O) | 119.3 grams |

Procedure:

The 2,2-thiodipropanol and the sulfuric acid were stirred together under nitrogen in a 2 l. glass reactor fitted with a stirrer, thermometer, addition funnel, and a fractionating distillation column. The temperature of the stirred material was rapidly brought to 100° C., at which point, the slow addition of a mixture of the 2-mercaptoethanol and the HEHS was begun. The addition was complete after 3 hours. The temperature was then increased to 120° C. and the water formed allowed to distill. When the mercaptan equivalent reached 33,000 g/eg. further reaction was carried out under vacuum until analysis showed a hydroxyl number of 10 or less. The resulting polythioether was a turbid, colorless liquid.

The barium hydroxide slurry was then added to the sulfuric acid containing polythioether. This mixture was stirred at 98° C. for approximately 3 hours or until analysis showed the mixture to be neutral. The polythioether polymer was then dried and filtered to remove the barium sulfate formed. The neutralized polythioether was a slightly turbid, colorless liquid with a viscosity of 37 poise. The molecular weight, as determined by GPC, was 1840.

EXAMPLE 5

Synthesis of chain extended dihydroxy monomer and condensation thereof to a linear hydroxyl terminated polythioether.

| | |
|---|---|
| 2,2'-Thiodipropanol | 577 grams |
| HE-2-HPS | 523 grams |
| 2-Mercaptoethanol | 900 grams |
| Sulfuric acid (50% w/w) | 20 grams |
| Barium hydroxide (19.3 grams Ba(OH)$_2$.H$_2$O in 100 grams H$_2$O) | 119.3 grams |

Procedure:

The 2,2'-thiodipropanol, HE-2-HPS and the 50% sulfuric acid were stirred together under nitrogen in a 2 l. glass reactor fitted with a stirrer, thermometer, addition funnel and a fractionating distillation column. The temperature of the stirred material was rapidly brought to 100° C., at which point, the slow addition of the 2-mercaptoethanol was begun. The addition was complete after 4 hours. The temperature was then increased to 120° C. and the water formed allowed to distill. After 3 hours analysis showed a hydroxyl number of 95. Further reaction was carried out under vacuum. After ½ hour analysis showed a hydroxyl number of 55. The resulting polythioether was a turbid, slightly thixotropic, colorless liquid.

The barium hydroxide slurry was then added to the sulfuric acid containing polythioether. This mixture was stirred at 98° C. for approximately 3 hours or until analysis showed the mixture to be neutral. The polythioether polymer was dried and filtered to remove the barium sulfate formed. The neutralized polythioether was a slightly turbid, colorless liquid with a viscosity of 125 poise.

EXAMPLE 6

Synthesis of 2,6,10-Trihydroxy-4,8-dithiaundecane (TDU).

| | |
|---|---|
| 1-Chloro-2,3-epoxypropane | 463 grams |
| 2-Mercaptopropanol | 922 grams |
| Sodium hydroxide | 200 grams |

Procedure:

The 2-Mercaptopropanol (10.0 moles) and the sodium hydroxide (5.0 moles) were stirred together in a 2 liter glass flask fitted with a stirrer, thermometer, and reflux condenser. The exotherm was controlled by a water bath.

This mixture was added dropwise, with stirring, to a 5 liter glass reactor containing the 1-Chloro-2,3-epoxypropane. This reactor was fitted with a stirrer, thermometer, and reflux condenser. The exotherm was controlled by a water bath so that the temperature of the contents did not rise above 100° C. After the mercaptan mixture had been added and the exotherm had subsided, the mixture was heated at 80° C. for 5 hours. The residual, unreacted mercaptan was found to be 0.1%. The crude mixture was washed twice with 2 volumes of saturated sodium bicarbonate and twice with 2 volumes of distilled water. The resulting material contained approximately 75% 2,6,10-Trihydroxy-4,8-dithiaundecane, a viscous, colorless liquid.

EXAMPLE 7

Synthesis of branched hydroxyl terminated polythioether.

| | |
|---|---|
| 2,2'-Thiodipropanol | 852 grams |
| 2-Mercaptoethanol | 1015 grams |
| TDU | 133 grams |
| H$_2$SO$_4$ (50% w/w) | 20 grams |
| Barium hydroxide (19.3 grams Ba(OH)$_2$.H$_2$O in 100 grams H$_2$O) | 119.3 grams |

Procedure:

The 2,2'-thiodipropanol, TDU, and the sulfuric acid were stirred together under nitrogen in a 2 l. glass reactor fitted with a stirrer, thermometer, addition funnel, and a fractionating distillation column. The temperature of the stirred material was rapidly brought to 100° C., at which point, the slow addition of the 2-mercaptoethanol was begun. The addition was complete after 4 hours. The temperature was then increased to 120° C. and the water allowed to distill. After 3 hours, analysis showed a hydroxyl number of 122. Further reaction was carried out under vacuum. After 2 hours analysis showed the hydroxyl number to be 58. The resulting polythioether was a turbid, viscous, colorless liquid.

The barium hydroxide slurry was then added to the sulfuric acid containing polythioether. This mixture was stirred at 98° C. for approximately 3 hours or until analysis showed the mixture to be neutral. The polythioether polymer was dried and filtered to remove the barium sulfate formed. The neutralized polythioether was a turbid, colorless liquid with a viscosity of 895 poise.

EXAMPLE 8

Synthesis of branched thiol terminated polythioether.

| | |
|---|---|
| 2,2'-Thiodipropanol | 1078 grams |
| 1,2-Dimercaptoethane | 814 grams |
| TDU | 108 grams |
| Sulfuric Acid (50% w/w) | 20 grams |
| Barium hydroxide (19.3 grams Ba(OH)$_2$.H$_2$O in 100 grams H$_2$O) | 119.3 grams |

Procedure:

The 2,2'-thiodipropanol, the 1,2-dimercaptoethane, the TDu, and the sulfuric acid were stirred together under nitrogen in a 2 l. glass reactor fitted with a stirrer, thermometer, and a fractionating distillation column. The temperature of the stirred material was brought to 110° C. and the water formed was allowed to distill. After five hours the mercaptan equivalent was 900 g/eq. Further reaction was carried out under vacuum. After 5 hours analysis showed a mercaptan equivalent of 1380 g/eq and no hydroxyl remaining in the infra-red spectrum. The resulting polythioether was a slightly turbid, colorless liquid.

The barium hydroxide slurry was then added to the sulfuric acid containing polythioether. This mixture was stirred at 98° C. for approximately 3 hours or until analysis showed the mixture to be neutral. The polythioether polymer was dried and filtered to remove the barium sulfate formed. The neutralized polythioether was a slightly turbid, colorless liquid with a viscosity of 175 poise. The polythioether when mixed with a manganese dioxide curative; yielded a rubber of 16 Rex.

EXAMPLE 9

Synthesis of linear hydroxyl terminated polythioether.

| | | |
|---|---|---|
| 2,2'-Thiodipropanol | 1279 | grams |
| 1,2-Dimercaptoethane | 721 | grams |
| Sulfuric acid (50% w/w) | 20 | grams |
| Barium hydroxide (19.3 grams Ba(OH)$_2$.H$_2$O in 100 grams H$_2$O) | 119.3 | grams |

Procedure:

The 2,2'-thiodipropanol, the 1,2-dimercaptoethane and the sulfuric acid were stirred together under nitrogen in a 2 l. glass reactor fitted with a stirrer, thermometer, and a fractionating distillation column. The temperature of the stirred material was brought to 110° C. and the water formed was allowed to distill. After three hours the mercaptan equivalent was 2300 g/eq. Further reaction was carried out under vacuum. After four hours at 125 torr analysis showed a mercaptan equivalent of 32,000 g/eq and a hydroxyl member of approximately 120. After one and a half additional hours at 10 torr analysis showed a mercaptan equivalent of 280,000 g/eq and a hydroxyl number of 55. The resulting polythioether was a turbid, viscous, colorless liquid.

The barium hydroxide slurry was then added to the sulfuric acid containing polythioether. This mixture was stirred at 98° C. for approximately 3 hours or until analysis showed the mixture to be neutral. The polythioether polymer was dried and filtered to remove the barium sulfate formed. The neutralized polythioether was a turbid, colorless liquid with a viscosity of 310 poise.

EXAMPLE 10

Synthesis of linear thiol terminated polythioether.

| | | |
|---|---|---|
| 2,2'-Thiodipropanol | 1204 | grams |
| 1,2-Dimercaptoethane | 796 | grams |
| Sulfuric Acid (50% w/w) | 20 | grams |
| Barium Hydroxide (19.3 grams Ba(OH)$_2$.H$_2$O in 100 grams H$_2$O) | 119.3 | grams |

Procedure:

The 2,2'-thiodipropanol, the 1,2-dimercaptoethane, and the sulfuric acid were stirred together under nitrogen in a 2 l. glass reactor fitted with a stirrer, thermometer, and a fractionating column. The temperature of the stirred material was brought to 110° C. and the water formed was allowed to distill. After eight hours the mercaptan equivalent was 1180 g/eq. Further reaction was carried out under vacuum. After 2 hours analysis showed a mercaptan equivalent of 1980 and no hydroxyl remaining in the infra-red spectrum. The resulting polythioether was a turbid, colorless liquid.

The barium hydroxide slurry was then added to the sulfuric acid containing polythioether. This mixture was stirred at 98° C. for approximately 3 hours or until analysis showed the mixture to be neutral. The polythioether polymer was dried and filtered to remove the barium sulfate formed. The neutralized polythioether was a turbid, colorless liquid with a viscosity of 235 poise. The polythioether when mixed with a Novalac epoxy of functionality 2.2 cured to a rubber of 14 Rex.

EXAMPLE 11

Synthesis of linear thiol terminated polythioether.

| | | |
|---|---|---|
| 2,2'-Thiodipropanol | 1065 | grams |
| 2,2'-Dimercaptodiethyl sulfide | 581 | grams |
| 1,2-Dimercaptoethane | 354 | grams |
| Sulfuric acid (50% w/w) | 20 | grams |
| Barium hydroxide (19.3 grams Ba(OH)$_2$.H$_2$O in 100 grams H$_2$O) | 119.3 | grams |

Procedure:

The 2,2'-thiodipropanol, the 2,2'-dimercaptodiethyl sulfide, the 1,2-dimercaptoethane and the sulfuric acid were stirred together under nitrogen in a 2 l. glass reactor fitted with a stirrer, thermometer, and a fractionating distillation column. The temperature of the stirred material was brought to 110° C. and the water formed was allowed to distill. After 5 hours the mercaptan equivalent was 1000 g/eq. Further reaction was carried out under vacuum. After 3½ hours analysis showed a mercaptan equivalent of 2160 g/eq and no hydroxyl remaining in the infra-red spectrum. The resulting polythioether was a slightly turbid, colorless liquid.

The barium hydroxide slurry was then added to the sulfuric acid containing polythioether. This mixture was stirred at 98° C. for approximately 3 hours or until analysis showed the mixture to be neutral. The polythioether polymer was dried and filtered to remove the barium sulfate formed. The neutralized polythioether was a colorless liquid with a viscosity of 115 poise. The polythioether when mixed with a Novalac type epoxy with a functionality of 2.2 cured to a rubber of 15 Rex.

EXAMPLE 12

Synthesis of branched thiol terminated polythioether.

| | | |
|---|---|---|
| 2,2'-Thiodipropanol | 855 | grams |
| 2,2'-Dimercaptodiethyl sulfide | 1059 | grams |
| TDU | 86 | grams |
| Sulfuric acid (50% w/w) | 20 | grams |
| Barium hydroxide (19.3 grams Ba(OH)$_2$.H$_2$O in 100 grams H$_2$O) | 119.3 | grams |

Procedure:

The 2,2'-thiodipropanol, the 2,2'-dimercaptodiethyl sulfide, the TDU, and the sulfuric acid were stirred together under nitrogen in a 2 l. glass reactor fitted with a stirrer, thermometer, and a fractionating distillation column. The temperature of the stirred material was brought to 110° C. and the water formed was allowed to distill. After five hours the mercaptan equivalent was 950 g/eq. Further reaction was carried out under vacuum. After 3 hours analysis showed a mercaptan equivalent of 1450 g/eq and no hydroxyl remaining in the infra-red spectrum. The resulting polythioether was a slightly turbid, colorless liquid.

The barium hydroxide slurry was then added to the sulfuric acid containing polythioether. This mixture was stirred at 98° C. for approximately 3 hours or until analysis showed the mixture to be neutral. The polythioether polymer was dried and filtered to remove the barium sulfate formed. The neutralized polythioether was a slightly turbid, colorless liquid with a viscosity of 150 poise. The polythioether when mixed with a manganese dioxide curative yielded a rubber of 17 Rex.

EXAMPLE 13

Synthesis of 1,3,5 Tri-(betamercaptoethyl sulfide)triazine (TMES).

| | |
|---|---|
| Dimercaptodiethyl sulfide | 80 grams |
| Sodium hydroxide (50 wt. % aqueous solution) | 40 grams |
| Cyanuric chloride | 30 grams |

Procedure:
The dimercaptodiethyl sulfide and sodium hydroxide were placed in a three neck flask. Cyanuric acid was slowly added with vigorous stirring and under a stream of nitrogen. The temperature of the exothermic reaction was not allowed to rise above 90° C. The material was kept between 75° C. and 90° C. for one and one-half hours, then cooled, extracted with toluene and vacuum evaporated to remove the solvent. The resulting material was found to have a mercaptan equivalent of 181.6.

EXAMPLE 14

Synthesis of 1,3,5 Tri-(betahydroxypropyl sulfide)-triazine (THPS).

| | |
|---|---|
| 1-mercapto-2-propanol | 96 grams |
| Sodium hydroxide | 40 grams |
| Cyanuric chloride | 63 grams |

Procedure:
The sodium hydroxide was dissolved in 60 grams of water and placed in a three neck flask to which the 1-mercapto-2-propanol was added. The cyanuric chloride was added to this mixture with heating to about 80° C. for three hours. Methylisobutylketone was then added, the salt filtered off and the residue evaporated under vacuum to remove the solvent. A viscous liquid was obtained.

EXAMPLE 15

Synthesis of branched thio-terminated polythioether.

| | |
|---|---|
| 1-Mercapto-2-propanol | 5 grams |
| TMES | 2.4 grams |
| Polystyrene-sulfonic acid | 5 grams |
| Sulfuric acid (50% w/w) | 0.2 grams |

Procedure:
The polystyrene-sulfonic acid used in this example was prepared from Amberlite IR(20) which is an ion exchange resin of the sodium salt of polystyrene-sulfonic acid. The hydrogen form of this ionic exchange resin was prepared by contacting the ion exchange resin with concentrated hydrochloric acid and then washing the acid form with water and drying. The thus prepared hydrogen version of Amberlite IR(20), which is a powder was added to the 1-mercapto-2-propanol. The mixture was initially stirred for 16 hours at 70° C. in a closed container, with intermittent vacuum applied to keep the ion exchange resin powder in a dispersed, non-agglomerated condition. When the hydroxyl number had reached 60, the batch was extracted with toluene, filtered, the solvent removed and the TMES was added along with the sulfuric acid. After heating for 4 hours at about 107° C. the thus obtained polymer was washed with methanol and the polymer cured to a hardness of 22 Rex and showed no hydroxyl bond.

EXAMPLE 16

Synthesis of 2-hydroxy-9-mercapto-4,7-dithianonane (HMN).

| | |
|---|---|
| Dimercapto diethyl sulfide | 64 grams |
| Propylene oxide | 23.2 grams |

Procedure:
To the dimercapto diethyl sulfide was added one drop of tetramethyl guanidine. The mixture was heated to a temperature of between 30° C. and 40° C. and the propylene oxide was added, with stirring, dropwise over several hours and the HMN recovered.

EXAMPLE 17

Synthesis of branched thiol-terminated polythioether.

| | |
|---|---|
| HMN | 25.4 grams |
| TMES | 3.6 grams |
| Sulfuric acid (40% w/w) | 0.4 grams |

Procedure:
The HMN, TMES and sulfuric acid were mixed and heated overnight at 100° C. and then flushed with dry nitrogen while stirring for 2 hours. The mercaptan equivalent was 600. After boiling with water and isolating with toluene extraction the product was cured with trimethylol propane diacrylate to a very hard rubber.

EXAMPLE 18

Synthesis of branched thio-terminated polythioether.

| | |
|---|---|
| 1-Mercapto-2-propanol | 9.7 grams |
| Dimercapto diethyl sulfide | 0.7 grams |
| TDU | 0.36 grams |
| Polystyrene sulfonic acid | 0.4 grams |

Procedure:
The 1-mercapto-2-propanol, dimercapto diethyl sulfide, TDU and polystyrene sulfonic acid (as a catalyst) were mixed together and heated in a sealed container at about 115° C. and stirred with a magnetic stirrer. The temperature was reduced to about 100° C. and a stream of nitrogen used to remove the water for 6 hours. The polymer was purified by washing with hot water, adding toluene, centrifuging and vacuum drying. The polymer had a mercaptan equivalent of 2533.

EXAMPLE 19

Synthesis of linear hydroxyl terminated polythioether.

| | |
|---|---|
| 1-Mercapto-2-propanol | 100 grams |
| Thiodipropanol | 7 grams |
| Sulfuric acid (50% w/w) | 1 grams |

Procedure:
A mixture of the 1-mercapto-2-propanol and thiodipropanol was made and then there was added, with stirring, the sulfuric acid. The resulting mixture was refluxed for 48 hours with slow removal of the water reaction product. The resulting polymer was washed and solvent extracted with toluene. The polymer had a hydroxyl equivalent of 1500 and cured to a very tough elastomer with a trifunctional aromatic isocyanate.

We claim:

1. A liquid polythioether containing no oxygen in the polymeric backbone which is non-crystallizing and water and fuel resistant having the following formula:

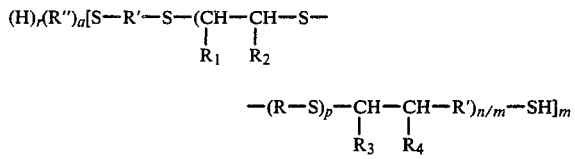

wherein each of $R_2$ and $R_3$ is hydrogen or lower alkyl, each of $R_1$ and $R_4$ is lower alkyl, R is lower alkylene or lower alkyl thioether, p is 0 to 3, n is from about 8 to 200, r is 0 or 1, a is 0 or 1, m is 1, 3 or 4, the sum of a and r being 1, when m is 1, r is 1 and when m is 3 or 4, a is 1, R' is an organic divalent radical having no chemically reactive groups of an organic primary dimercaptan having the formula R'—(SH)$_2$, each mercaptan group being primary and R" is a tri- or tetravalent organic fragment having no chemically reactive groups of the organic compound having the formula R"—(Z)$_q$ wherein Z is a secondary hydroxyl located beta to a sulfur atom or a primary mercaptan group and q is 3 or 4.

2. A liquid polythioether according to claim 1 wherein a is 1 and m is 3 or 4.

3. A liquid polythioether according to claim 2 wherein R' is lower alkylene, loweralkylene thioether or aromatic.

4. A liquid polythioether according to claim 3 wherein aromatic is alkyl aromatic or hetero-aromatic.

5. A liquid polythioether according to claim 2 wherein R" is alkylene of from four to thirty carbon atoms, lower alkyl aryl or lower alkyl heterocyclic.

6. A liquid polythioether according to claim 5 wherein R" has a molecular weight of less than about 500.

7. A liquid polythioether having no oxygen in the polymeric backbone and 2 to 4 terminal secondary hydroxyl groups which is non-crystallizing and water and fuel resistant and has the following formula:

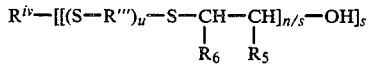

wherein $R_6$ is hydrogen or lower alkyl, $R_5$ is lower alkyl, s is 2, 3 or 4, n is from about 8 to 200, u is 0 or 1, $R^{iv}$ is a di-, tri- or tetravalent organic fragment having no chemically reactive groups of the organic polyhydroxy compound $R^{iv}$—(OH)$_s$ wherein each hydroxyl group is secondary and located beta to a sulfur atom, and R''' is a divalent organic radical having no chemically reactive groups.

8. A liquid polythioether according to claim 7 wherein s is 2.

9. A liquid polythioether according to claim 8 wherein R''' is lower alkylene or lower alkylene thioether.

10. A liquid polythioether according to claim 8 wherein $R^{iv}$ is from six to 20 carbon atoms.

11. A liquid polythioether according to claim 7 wherein s is 3 or 4.

12. A liquid polythioether according to claim 11 wherein $R^{iv}$ is alkylene of from 8 to 20 carbon atoms.

13. A liquid polythioether according to claim 12 wherein $R^{iv}$ has a molecular weight less than about 500.

14. A liquid polythioether containing no oxygen and 2 to 4 terminal primary mercaptan groups which is non-crystallizing and water and fuel resistant and has the formula:

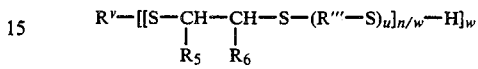

wherein $R_5$ is lower alkyl, $R_6$ is hydrogen or lower alkyl, u is 0 or 1, n is from about 8 to 200, w is 2, 3 or 4, R''' is a divalent organic radical having no chemically active groups and $R^v$ is the organic fragment of the polymercaptan compound $R^v$—(SH)$_w$ wherein each mercaptan group is primary.

15. A liquid polythioether according to claim 14 wherein R''' is lower alkylene or lower alkyl thioether.

16. A liquid polythioether according to claim 15 wherein $R^v$ is alkylene of from four to thirty carbon atoms, lower alkyl or lower alkyl heterocyclic.

17. A liquid polythioether according to claim 16 wherein w is 3 or 4.

18. A method for producing a liquid polythioether which is non-crystallizing, is water and fuel resistant and has a molecular weight of between about 900 to about 25,000 which comprises forming a reaction admixture of (i) a di-secondary beta thioether diol reactant having the formula:

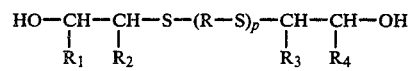

wherein each of $R_2$ and $R_3$ is hydrogen or lower alkyl, each of $R_1$ and $R_4$ is lower alkyl, R is lower alkylene or lower alkyl thioether and p is 0 to 3, (ii) an organic primary dimercaptan reactant having the formula:

wherein R' is a divalent organic radical and the mercaptan groups are primary, (iii) a catalytic effective amount of a non-oxidizing, strong acid dehydration catalyst in a sufficient amount of water to prevent said catalyst from oxidizing the reactants; and (iv) a branching agent reactant of the formula:

wherein q is 3 or 4 and R" is a tri- or tetravalent organic radical having no chemically reactive groups, Z is a secondary hydroxyl located beta to a sulfur atom or a primary mercaptan group; heating said reactants to a temperature of between about 90° C. and 140° C. to react substantially only the primary mercaptan group with the hydroxyl group and removing a sufficient amount of the water formed by the reaction to prevent the reaction from terminating until a liquid polythioether is formed having a molecular weight of between about 900 to about 25,000.

19. A method according to claim 18 wherein the non-oxidizing strong acid catalyst is sulfuric acid or sulfonic acid.

20. A method according to claim 19 wherein an excess of reactant (i) is used relative to reactant (ii) to produce a liquid polythioether having 2 to 4 terminal primary mercaptan groups.

21. A method according to claim 19 wherein an excess of reactant (ii) is used relative to reactant (i) to produce a liquid polythioether having 2 to 4 terminal hydroxyl groups.

22. A method according to claim 19 wherein reactant (iv) is not present to produce a linear liquid polythioether.

23. A method according to claim 19 wherein reactant (iv) is present in an amount sufficient to produce a branched liquid polythioether.

24. A method according to claim 23 wherein Z is a secondary hydroxyl located beta to a sulfur atom.

25. A method according to claim 23 wherein Z is a primary mercaptan.

26. A method for producing a liquid polythioether which is non-crystallizing, is water and fuel resistant and has a molecular weight of between about 900 to about 25,000, which comprises forming a reaction admixture of (i) a secondary beta-hydroxy mercaptan reactant having the formula:

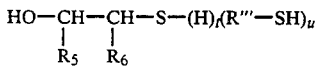

wherein —SH is primary, $R_5$ is lower alkyl, $R_6$ is hydrogen or lower alkyl, t and u are each 0 or 1 the sum of u and t being 1, when t is 1, $R_6$ is hydrogen, and $R'''$ is divalent organic radical; (ii) a catalytic effective amount of a non-oxidizing, strong acid dehydration catalyst in a sufficient amount of water to prevent said catalyst from oxidizing the reactants; and (iii) a polyhydroxy initiator reactant having the formula:

wherein $R^{iv}$ is a di-, tri- or tetravalent organic compound having no chemically reactive groups, s is 2, 3 or 4 and each of the —OH groups are secondary and beta to a sulfur atom; or (iv) a polymercaptan initiator reactant having the formula:

wherein $R^v$ is an organic radical having no chemically reactive groups, the —(SH) groups are primary and w is 2, 3 or 4; heating said reactants to a temperature of between about 90° C. and 140° C. to react substantially only the primary mercaptan group with the hydroxyl group and removing a sufficient amount of the water formed by the reaction to prevent the reaction from terminating until a liquid polythioether is formed having a molecular weight of between about 900 to about 25,000.

27. A method for producing a liquid polythioether according to claim 26 wherein the non-oxidizing strong acid dehydration catalyst is sulfuric acid or sulfonic acid.

28. A method according to claim 27 wherein reactant (iii) is present and s is 2 to produce a linear polythioether.

29. A method according to claim 27 wherein reactant (iii) is present and s is 3 or 4 to produce a branched polythioether.

30. A method according to claim 27 wherein reactant (iv) is present and w is 2 to produce a linear polythioether.

31. A method according to claim 27 wherein reactant (iv) is present and w is 3 or 4 to produce a branched liquid polythioether.

32. A method according to claim 27 wherein t is 1.

33. A method according to claim 27 wherein t is 0 and $R'''$ is lower alkylene or lower alkylene thioether.

34. A method according to claim 28 or 29 wherein $R^{iv}$ has a molecular weight of less than 500 and has from six to twenty carbon atoms.

35. A method according to claim 30 wherein $R^v$ is lower alkylene, lower alkylene thioether and aromatic.

36. A method according to claim 31 wherein $R^v$ has a molecular weight less than 500 and is alkylene of from four to thirty carbon atoms, lower alkyl aryl or lower alkyl heterocyclic.

* * * * *